(12) United States Patent
Scott

(10) Patent No.: US 8,278,942 B2
(45) Date of Patent: *Oct. 2, 2012

(54) SELF-CHECKING ANALYZER METHOD AND SYSTEM USING REFLECTED POWER/INSERTION LOSS

(75) Inventor: Bentley N. Scott, Garland, TX (US)

(73) Assignee: Phase Dynamics, Inc., Richardson, TX (US)

( * ) Notice: Subject to any disclaimer, the term of this patent is extended or adjusted under 35 U.S.C. 154(b) by 276 days.

This patent is subject to a terminal disclaimer.

(21) Appl. No.: 12/416,878

(22) Filed: Apr. 1, 2009

(65) Prior Publication Data

US 2009/0256579 A1  Oct. 15, 2009

Related U.S. Application Data

(60) Provisional application No. 61/072,613, filed on Apr. 1, 2008.

(51) Int. Cl.
*G01R 27/04* (2006.01)

(52) U.S. Cl. ........................................ 324/643; 324/634

(58) Field of Classification Search .......... 324/640–643, 324/664, 689, 634; 250/301; 73/61.79, 861.04
See application file for complete search history.

(56) References Cited

U.S. PATENT DOCUMENTS 7,135,870 B2 * 11/2006 Mohajer et al. ............... 324/639
2008/0234574 A1 * 9/2008 Hancock et al. ............... 600/430

* cited by examiner

*Primary Examiner* — Jermele M Hollington
*Assistant Examiner* — Alesa Allgood

(57) ABSTRACT

A self-checking analyzer system is provided according to an embodiment of this disclosure. The analyzer system includes a pipeline for receiving a multi-phase fluid flow. The analyzer system also includes a first measuring device configured to provide a first reflected power/insertion loss measurement corresponding to the multi-phase fluid flow, and a second measuring device differing in frequency response from the first measuring device and configured to provide a second reflected power/insertion loss measurement corresponding to the multi-phase fluid flow. The analyzer system is configured to validate the first reflected power/insertion loss measurement using the second reflected power/insertion loss measurement.

20 Claims, 13 Drawing Sheets

SELF-CHECKING ANALYZER METHOD AND SYSTEM USING REFLECTED POWER/INSERTION LOSS

CROSS-REFERENCE TO RELATED APPLICATION(S) AND CLAIM OF PRIORITY

The present application is related to U.S. Provisional Patent No. 61/072,613, filed Apr. 1, 2008, entitled "SELF CHECKING ANALYZER METHOD AND SYSTEM". Provisional Patent No. 61/072,613 is is hereby incorporated by reference into the present application as if fully set forth herein. The present application hereby claims priority under 35 U.S.C. §119(e) to U.S. Provisional Patent No. 61/072,613.

TECHNICAL FIELD OF THE INVENTION

The present application relates generally to analyzer systems and, more specifically, to water analyzer systems and methods.

BACKGROUND OF THE INVENTION

When water is pumped to the surface of the Earth along with crude petroleum oil, producers often attempt to determine the water content of the oil because water can corrode pipes and damage down-stream processing equipment. Furthermore, water has no value relative to the oil and in-fact can become a disposal or environmental problem wherever it is finally removed.

The accurate determination of the water content and the validation of the amount of water in crude petroleum oil is particularly important during the taxation of crude petroleum oil and the sale of crude petroleum oil, where the owner or seller of the oil does not want to pay taxes on water and the customer does not want to pay the price of oil for water. Such determinations and validations can be conducted on-line and off-line during petroleum processing.

Offline methods involve physically sampling the stream and analyzing it in a laboratory setting. In the petroleum industry, sampling is usually done using a composite sampler, which automatically opens a sample valve attached to a pipeline at a certain time interval to collect an aggregate sample into a sample container. The objective is to collect a sample which is representative of the entire lot of petroleum under consideration. After collection, the composite sample is usually picked up by a person and taken to a laboratory. The composite sample is then "sampled" to prepare aliquots, or sub-divisions of the composite sample, for each of the various characterizations, or analysis methods, being implemented.

However, composite petroleum samplers and the associated analytical methods have problems and disadvantages, such as meeting a desired accuracy for a given determination. For example, results for composite samplers are typically only available at the end of a batch or a test, and there is no recourse if something goes wrong with the sampling system during the sampling process. At the end of the sampling and analysis, only a single number is available to consider. Additionally, the exposure of personnel to hazardous liquids associated with processing the samples is undesirable. Thus, the petroleum industry has continued to seek other methods that provide the required accuracy, speed, and safety.

Accordingly, the use of rapid on-line instruments such as densitometers, capacitance probes, radio frequency probes, and microwave analyzers to measure the water content of petroleum products is becoming more common. In addition to providing increasingly accurate determinations of water content, real time water content results via on-line methods can provide beneficial operational advantages. Knowledge of when water becomes present in petroleum as it is being produced and the magnitude of the quantity of the water may provide an opportunity to remove the water before it reaches and corrodes or damages a transport pipeline, storage vessel, or shipping tanker. Additionally, real time data may show if the water is detected in several short periods of time or if it is present across the entire load of the petroleum. Furthermore, real time analyzers may be used as a comparison to the results provide by composite samplers. Finally, on-line measurements of, for example, physical and electrical properties via instrumentation reduces the need for human involvement in the process of characterizing a multiphase fluid mixture.

Despite the importance and advantages of on-line analyzers, they are typically subjected to long periods of use without recalibration although they may require recalibration due to things such as coating build up, leakage of o-ring seals, voltage changes with time, or component failure. Users of on-line analyzers often do not realize that the system has been compromised and requires recalibration until a manual sample of the multiphase fluid mixture is performed or the values produced by the analyzers are always zero, not changing, or indicate 100% water.

SUMMARY OF THE INVENTION

This disclosure provides a system and method for a self-checking analyzer.

A self-checking analyzer system is provided according to a first embodiment of this disclosure. The analyzer system includes a pipeline for receiving a multi-phase fluid flow. The analyzer system also includes a first measuring device configured to provide a first reflected power/insertion loss measurement corresponding to the multi-phase fluid flow, and a second measuring device differing in frequency response from the first measuring device and configured to provide a second reflected power/insertion loss measurement corresponding to the multi-phase fluid flow. The analyzer system is configured to validate the first reflected power/insertion loss measurement using the second reflected power/insertion loss measurement In particular embodiments of the measurement unit, the first measuring device is one of an oil oscillator and a water oscillator and the second first measuring device is the other.

In other particular embodiments of the measurement unit, the switch is a solid state switch.

In yet other particular embodiments of the measurement unit, the first reflected power/insertion loss measurement is used to determine a water content of the multi-phase fluid flow.

In yet further other particular embodiments of the measurement unit, the water content is derived from one or more calibration curves.

In still yet other particular embodiments of the measurement unit, the measurement unit is further configured to validate the first reflected power/insertion loss measurement by comparing a subsequent reflected power/insertion loss measurement of the first measuring device corresponding to free air with a calibrated value.

A self-checking analyzer system is provided according to a second embodiment of this disclosure. The analyzer system includes a pipeline for receiving a multi-phase fluid flow. The analyzer system also includes a first measuring device configured to provide a first reflected power/insertion loss measurement corresponding to the multi-phase fluid flow, and a second measuring device differing in frequency response from the first measuring device and configured to provide a second reflected power/insertion loss measurement corresponding to the multi-phase fluid flow. The analyzer system is configured to validate the first reflected power/insertion loss measurement using the second reflected power/insertion loss measurement.

In particular embodiments of the system, a switch configured to connect the first measuring device to an antenna element to obtain the first reflected power/insertion loss measurement and to connect the second oscillator to the antenna element to obtain the second reflected power/insertion loss measurement.

In other particular embodiments of the system, the switch is a solid state switch.

In yet other particular embodiments of the system, the first measuring device is one of an oil oscillator and a water oscillator and the second first measuring device is the other.

In yet further other particular embodiments of the system, the first reflected power/insertion loss measurement is used to determine a water content of the multi-phase fluid flow.

In still yet other particular embodiments of the system, the water content is derived from one or more calibration curves.

In yet further other particular embodiments of the system, the analyzer system is further configured to validate the first reflected power/insertion loss measurement by comparing a subsequent reflected power/insertion loss measurement of the first measuring device corresponding to free air with a calibrated value.

A method of validating a frequency response is provided according to a third embodiment of this disclosure. The method includes obtaining a first reflected power/insertion loss measurement corresponding to a multiphase fluid flow using a first measuring device, and obtaining a second reflected power/insertion loss measurement corresponding to the multiphase fluid flow using a second measuring device. The second measuring device differs in frequency response from the first measuring device. The method further includes validating the first reflected power/insertion loss measurement using the second reflected power/insertion loss measurement.

In particular embodiments of the method, the first measuring device is one of an oil oscillator and a water oscillator and the second first measuring device is the other.

In other particular embodiments of the method, the method further includes determining a first water content of the multiphase fluid flow using the first reflected power/insertion loss measurement.

In further particular embodiments of the method, the method further includes determining a second water content of the multiphase fluid flow using the second reflected power/insertion loss measurement, and validating the first water content using the second water content.

In yet other particular embodiments of the method, the first and second water contents are determined from one or more calibration curves.

In yet further other particular embodiments of the method, the method further includes validating the first reflected power/insertion loss measurement by comparing a subsequent reflected power/insertion loss measurement of the first measuring device corresponding to free air with a calibrated value.

In still yet other particular embodiments of the method, the first and second oscillators differ from one another in at least one of tuning elements, active devices, and matching circuitry.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION OF THE INVENTION

FIGS. 1 through 11, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged analyzer system.

Figure 1:
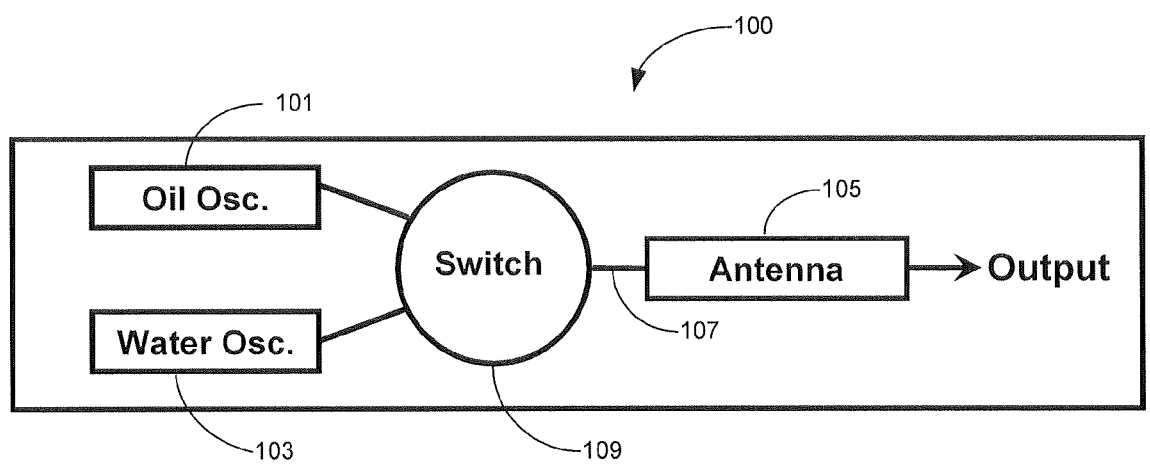
FIG. 1 illustrates an analyzing circuitry having two measurement systems that are independent of one another according to an embodiment of this disclosure.

FIG. 1 illustrates an example analyzing circuitry 100 according to this disclosure. The embodiment of the analyzing circuitry 100 shown in FIG. 1 is for illustration only. Other embodiments of the analyzing circuitry 100 could be used without departing from the scope of this disclosure.

FIG. 1 illustrates an analyzing circuitry having two measurement systems that are independent of one another according to an embodiment of this disclosure.

To alert a user that an analyzing system is not operating within calibrated values or that a failure has occurred, the analyzing circuitry 100 of FIG. 1 performs real time checking of the validity of the measurements of the analyzing system by using two measurement systems that are independent of one another. In this particular embodiment, the two measurement systems take the form of an oil oscillator 101 and a water oscillator 103. The oil oscillator 101 and the water oscillator 103 are independent of one another in terms of their tuning elements, active devices, and/or matching circuitry.

The analyzing circuitry 100 uses the measurement results of one oscillator to validate the measurement results of the other oscillator in real time. Because the two measurement systems are widely different in frequency response and reflected power/insertion loss, measurement results from the analyzing circuitry 100 will only be valid if both measuring systems produce measurement results that correspond to substantially the same water content.

In the embodiment shown in FIG. 1, the oil oscillator 101 and the water oscillator 103 both feed a coaxial antenna 105 via a coaxial line 107. The oil oscillator 101 and a water oscillator 103 are used to match energy into two emulsion types. In one case, the oil surrounds the water as an emulsion and is insulating like the oil. In some embodiments, this emulsion is perceived as a 50 ohm load in the line 107 at the beginning and decreases in impedance as the percentage of water increases in the emulsion. A solid state switch 109 is used to isolate one oscillator while connecting the other oscillator to the coaxial antenna 105. The solid state switch 109 may be, for example, a radio frequency (RF) switch.

Figure 2:
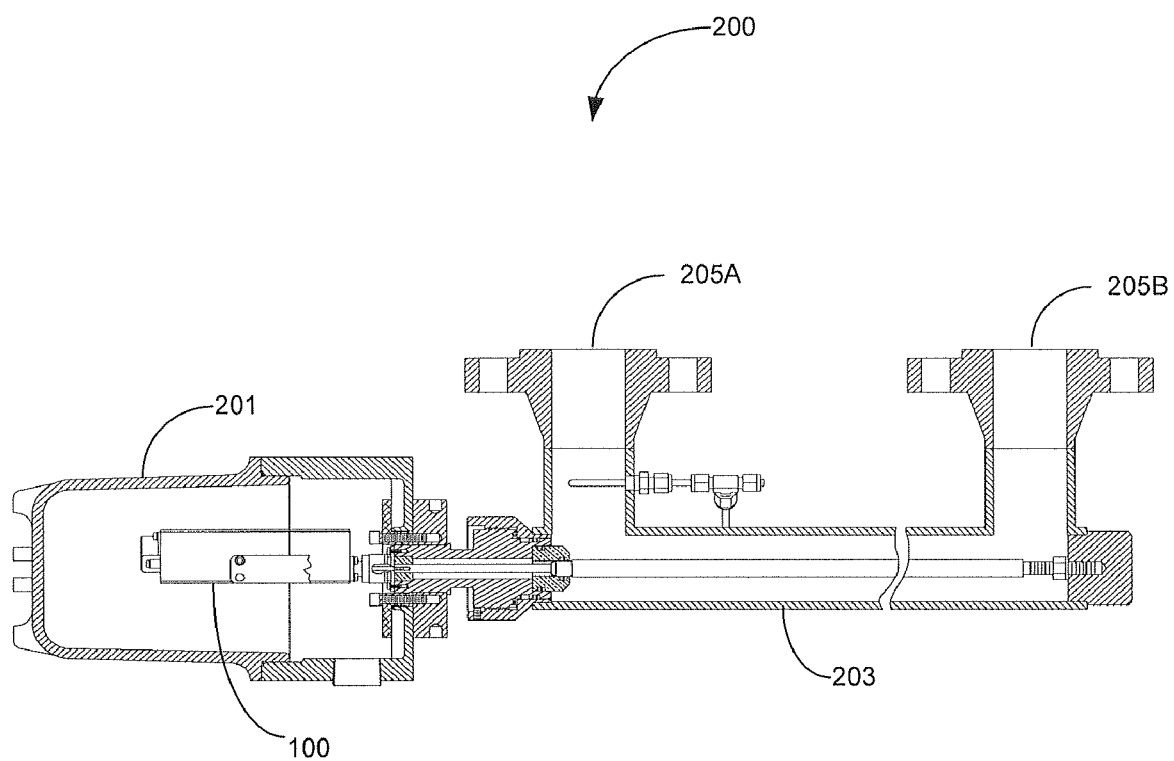
FIG. 2 illustrates a self-checking analyzer system having an analyzing circuitry according to an embodiment of this disclosure.

FIG. 2 illustrates an example self-checking analyzer system 200 according to this disclosure. The embodiment of the self-checking analyzer system 200 shown in FIG. 2 is for illustration only. Other embodiments of the self-checking analyzer system 200 could be used without departing from the scope of this disclosure.

FIG. 2 illustrates the self-checking analyzer system 200 having the analyzing circuitry 100 according to an embodiment of this disclosure.

In the embodiment shown in FIG. 2, the self-checking analyzer system 200 includes a measurement unit 201, which includes the analyzing circuitry 100 described above. The measurement unit 201 is in contact with a multiphase fluid flowing through a pipeline 203. The measurement unit 201 is able to measure the frequency response and the reflected power/insertion loss of the oil oscillator 101 and the water oscillator 103 to the multiphase fluid as the multiphase fluid flows through the pipeline 203. In this embodiment, the multiphase fluid enters and exits the pipeline 203 via flanges 205A and 205B.

Figure 3:
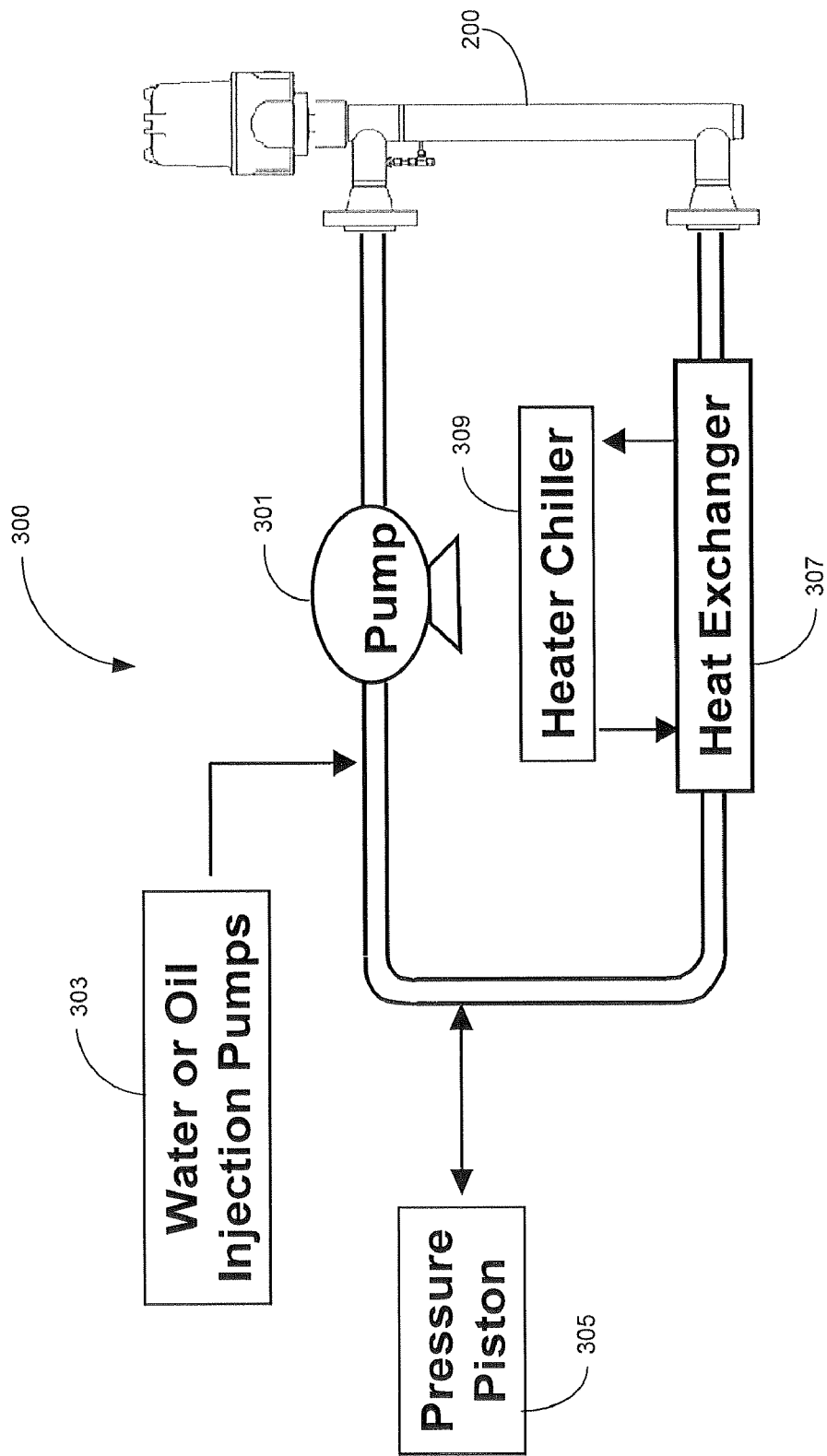
FIG. 3 illustrates a calibration flow loop for calibrating a self-checking analyzer system according to an embodiment of this disclosure.

FIG. 3 illustrates a calibration flow loop 300 for calibrating the self-checking analyzer system 200 according to an embodiment of this disclosure.

In the embodiment shown in FIG. 3, the calibration flow loop 300 includes, in addition to the self-checking analyzer system 200, a pump 301 for pushing a multiphase fluid mixture through the calibration flow loop 300. The calibration flow loop 300 further includes one or more water or oil injection pumps 303, a pressure piston 305, and a heat exchanger 307 in contact with a heater/chiller 309.

The calibration flow loop 300 is loaded with 100% oil or water and then water or oil is injected into the calibration flow loop 300 via injection pumps 303. The measurements taken as oil or water is injected into the calibration flow loop 300 are used to generate calibration curves for the oil oscillator 101 and the water oscillator 103 to indicate the frequency response and the reflected power/insertion loss of the self-checking analyzer system 200 at various water percentages.

Figure 4:
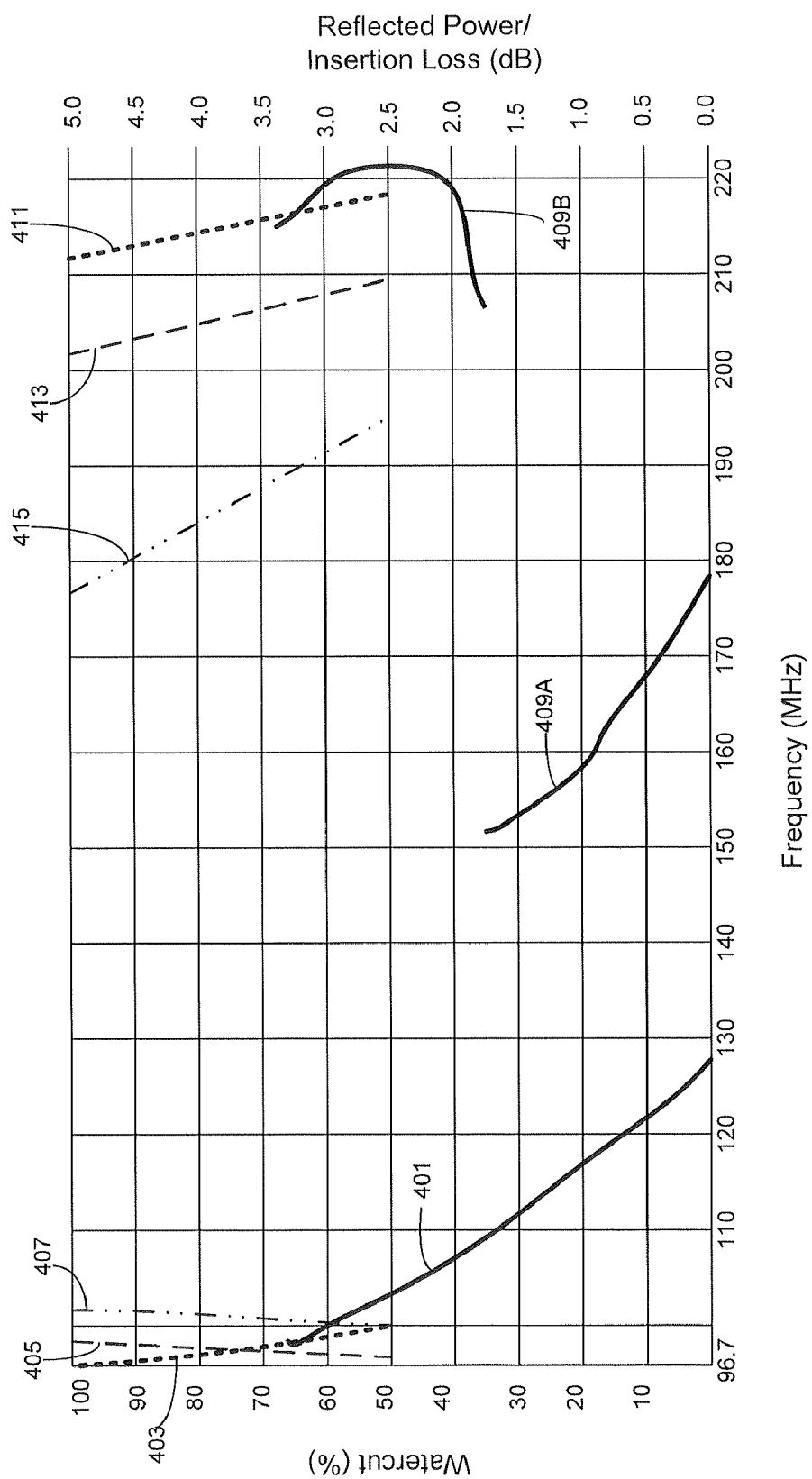
FIG. 4 illustrates an example of calibrations curves for an oil oscillator and a water oscillator according to an embodiment of this disclosure.

FIG. 4 illustrates an example of calibrations curves for the oil oscillator 101 and the water oscillator 103 according to an embodiment of this disclosure.

The left side of FIG. 4 shows the calibration curves for the oil oscillator 101, which range in frequency from 96.7 MHz to 128 MHz, and the right side of FIG. 4 shows the calibration curves for the water oscillator 103, which range in frequency from 152 MHz to 221.1 MHz.

With regard to the calibration curves for the oil oscillator 101 on the left side of FIG. 4, an oil emulsion curve 401 represents the oil emulsion for the oil oscillator 101. Because the water continuous phase (oil-in-water) is conductive due to the salinity of the water, a number of separate calibrations are made to obtain a family of salinity water emulsion curves 403, 405, and 407. For example, a salt water emulsion curve 403 was obtained at 0.1% salt content, a salt water emulsion curve 405 was obtained at 3% salt content, and a salt water emulsion curve 407 was obtained at 11% salt content.

With regard to the calibration curves for the water oscillator 103 on the right side of FIG. 4, an oil emulsion curve, indicated at 409A and 409B, represents the oil emulsion for the water oscillator 103. The oil emulsion curve 409 is discontinuous in that at 32% water the frequency is 152 MHz and jumps to 209.2 MHz at 33% water. The reason for this jump is that the technology of load-pulled oscillators provides for the returning of the frequency to a rollover frequency upon transitioning through 180 degrees of a phase shift. Because load-pulled oscillators designed and matched for the water phase are not normally used for the oil continuous emulsion phase, the discontinuity or jump in frequency does not interfere with the measurements. Like the oil oscillator 101 curves, the water oscillator 103 curves also include, for example, a salt water emulsion curve 411 obtained at 0.1% salt content, a salt water emulsion curve 413 obtained at 3% salt content, and a salt water emulsion curve 415 obtained at 11% salt content.

In one embodiment, validation of a measurement can be done simply by comparing the frequencies of the oil oscillator 101 and the water oscillator 103 with respect to the calibration curves corresponding to the same conditions of salinity and temperature. The frequencies for the oil oscillator 101 and the water oscillator 103 are independent of one another, and the frequency response of each will be affected differently due to any events (for example, problems with the liquid seals at the antenna, a bad component, or changes in the internal reference voltages) that may require the system to be recalibrated.

Figure 5:
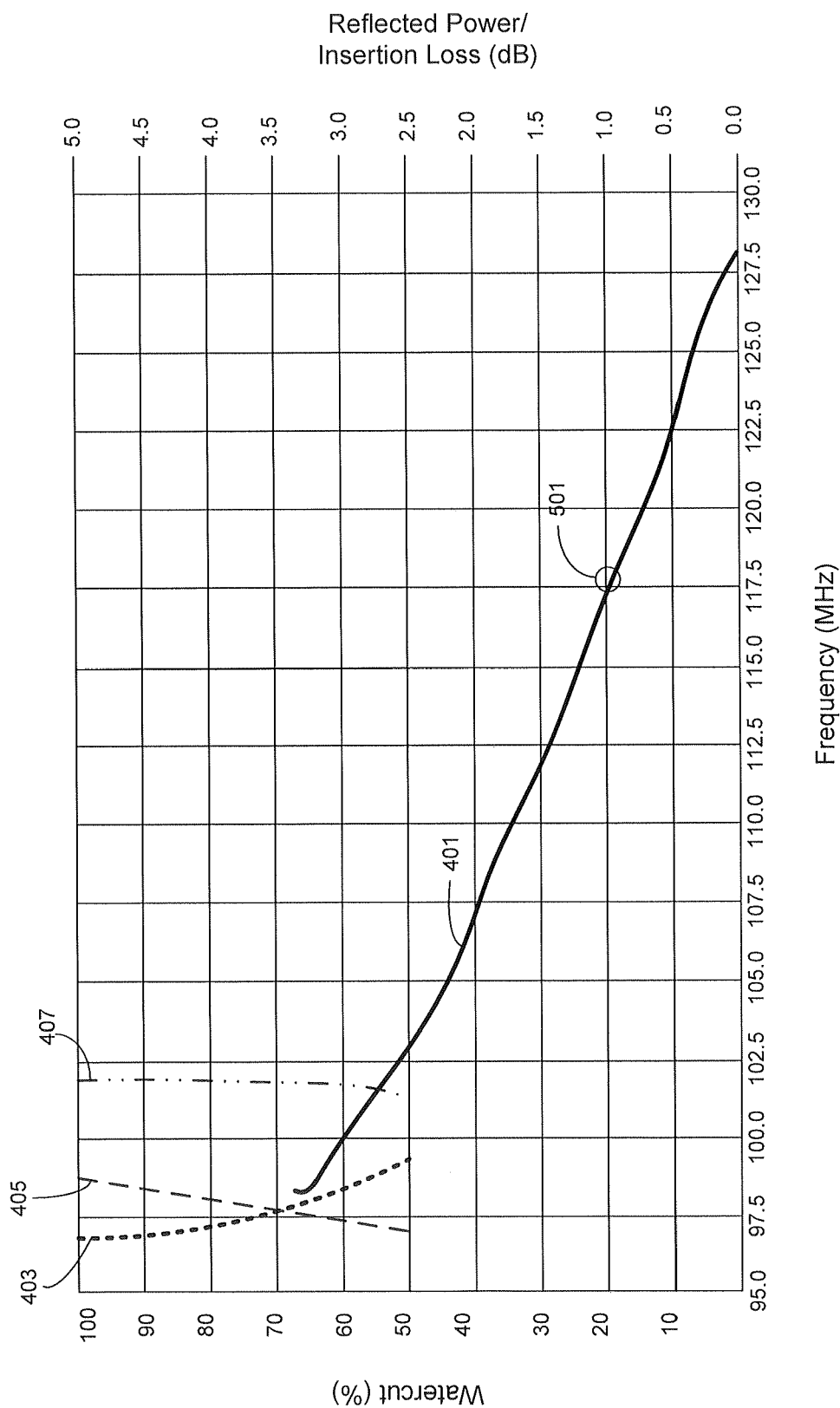
FIG. 5 illustrates calibration curves for an oil oscillator according to an embodiment of this disclosure.

FIG. 5 illustrates the calibration curves for the oil oscillator 101 according to an embodiment of this disclosure.

In one example, the solid state switch 109 has isolated the water oscillator 103 and connected the oil oscillator 101 to the coaxial antenna 105. If a frequency of 117.5 MHz is measured by the analyzing circuitry 100 in this example, then the water percentage would be determined to be 19.5% at a point 501 on the oil emulsion curve 401, which corresponds to 117.5 MHz.

Figure 6:
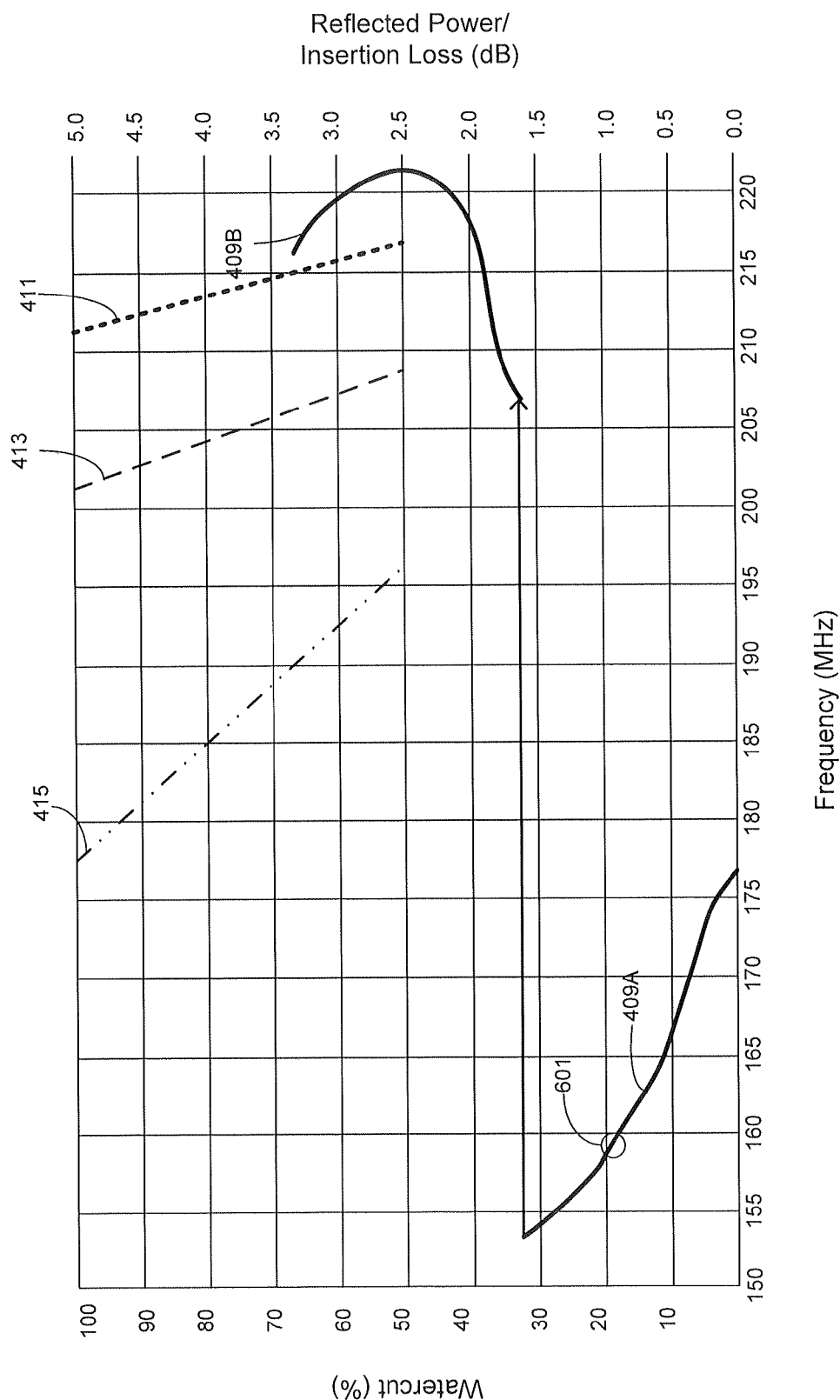
FIG. 6 illustrates calibration curves for a water oscillator according to an embodiment of this disclosure.

FIG. 6 illustrates the calibration curves for the water oscillator 103 according to an embodiment of this disclosure.

In the example shown in FIG. 6, a 19.5% watercut corresponds to a frequency of 159.5 MHz as indicated by a point 601 on the oil emulsion curve 409A. Accordingly, when the solid state switch 109 isolates the oil oscillator 101 and connects the water oscillator 103 to the coaxial antenna 105, the frequency measured by the analyzing circuitry 100 in this example should be approximately 159.5 MHz. If the measurement produced by the analyzing circuitry 100 at this time is approximately 159.5 MHz, then the self-checking analyzer system 200 would consider the 19.5% watercut measurement valid. Conversely, if the measurement produced by the analyzing circuitry 100 at this time is not approximately 159.5 MHz, then the self-checking analyzer system 200 would consider the 19.5% watercut measurement to be invalid. Errors in measurement can be displayed and could include the two frequencies and the differing water percentages that correspond to the two frequencies. The user would then be alerted that there is a system error. The user could then further check the frequency measurements or send the self-checking analyzer system 200 for repair.

Of course, the validity of the 19.5% watercut measurement also could be validated by comparing it with the watercut percentage that corresponds to the measured frequency of the water oscillator 103. In other words, the percentages are compared rather than the frequencies.

In another embodiment, the reflected power/insertion loss of the water oscillator 103 and the oil oscillator 101 is used to validate the integrity of the self-checking analyzer system 200. For example, as shown in FIGS. 5 and 6, a 19.5% watercut measurement also corresponds to a reflected power/insertion loss of approximately 1 dB. Therefore, unless both the water oscillator 103 and the oil oscillator 101 show a reflected power/insertion loss of approximately 1 dB, the 19.5% watercut measurement would not be considered valid.

Figure 7:
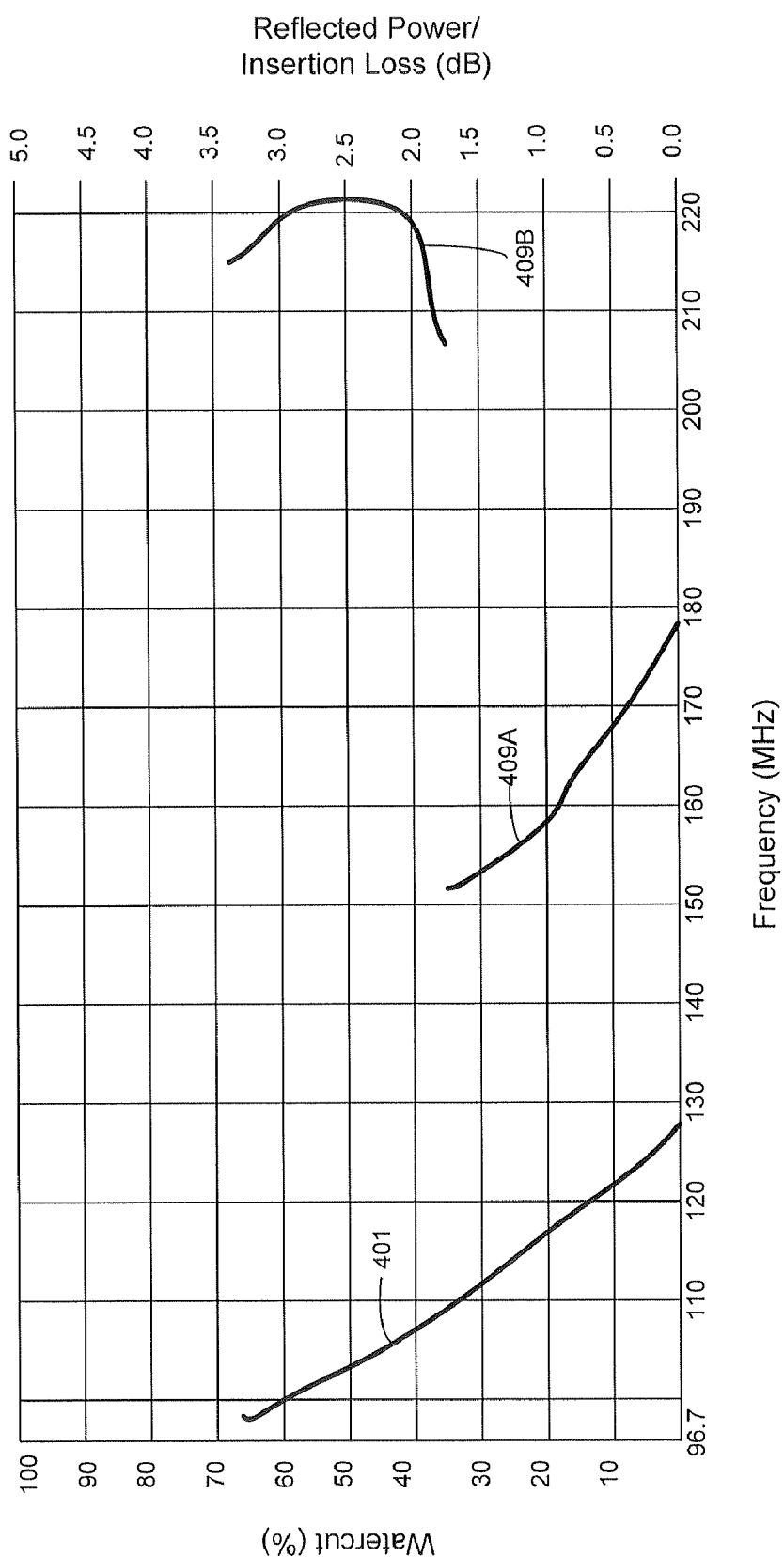
FIG. 7 illustrates oil continuous emulsion curves for a water oscillator and an oil oscillator according to an embodiment of this disclosure.

FIG. 7 illustrates the oil continuous emulsion curves 401 and 409 for the oil oscillator 101 and the water oscillator 103, respectively, according to an embodiment of this disclosure.

Figure 8:
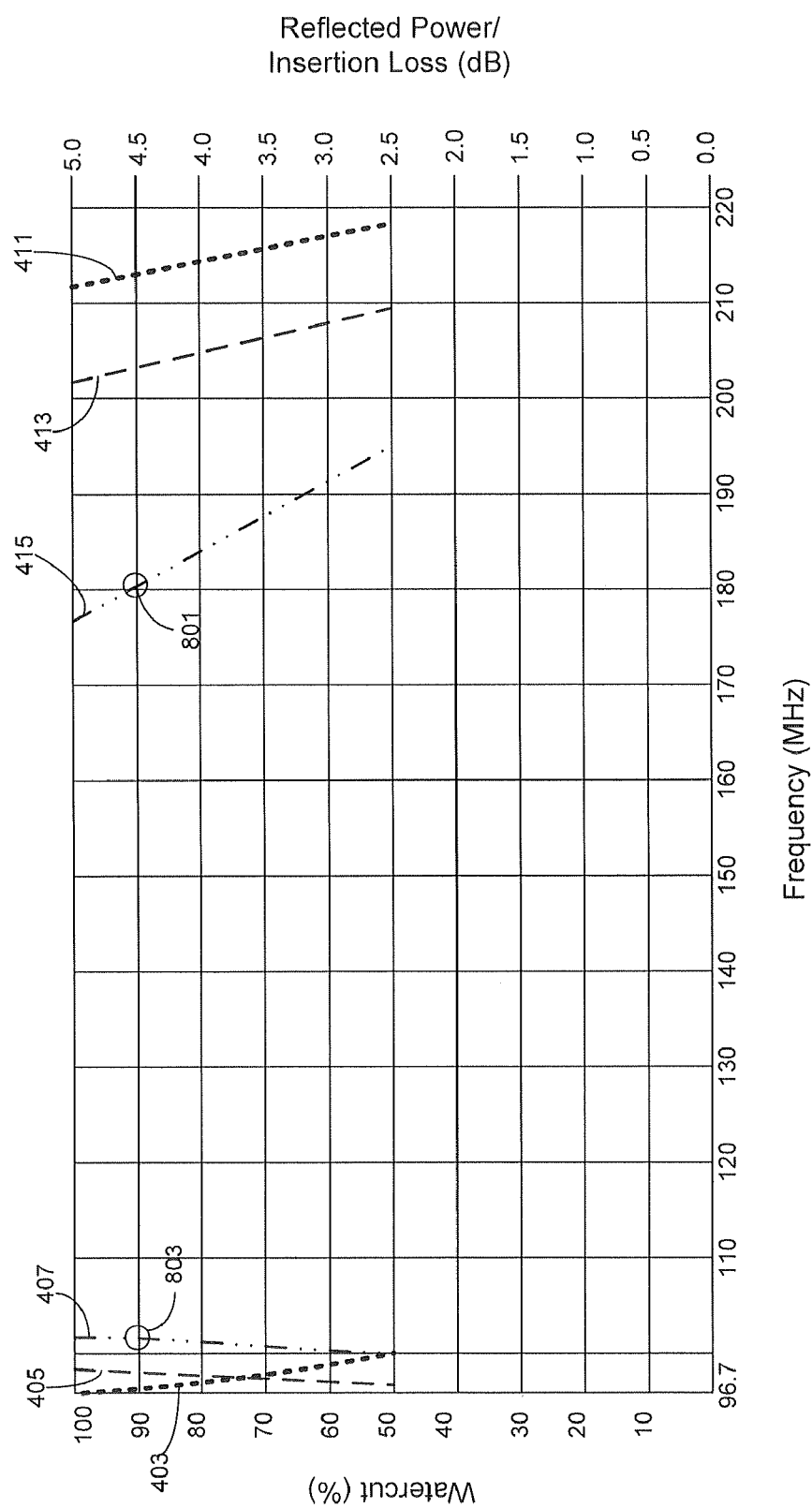
FIG. 8 illustrates extremes of water continuous emulsion curves for an oil oscillator and a water oscillator according to an embodiment of this disclosure.

FIG. 8 illustrates extremes of water continuous emulsion curves for the oil oscillator 101 and the water oscillator 103 according to an embodiment of this disclosure.

In this example, the self-checking analyzer system 200 is measuring a water continuous emulsion at 11% salinity. If the frequency measured by the water oscillator 103 is 180.88 MHz as indicated by a point 801 on the water emulsion curve 415 (11% salinity curve), then the water cut percentage would be determined to be 90% water, which corresponds to a point 803 on the water emulsion curve 407 (11% salinity curve) of the oil oscillator 101. The point 803 on the water emulsion curve 407 corresponds to a frequency of 102.08 MHz. In this case, a measurement from the oil oscillator 101 of, for example, 103 MHz would indicate that there is a problem with the integrity of the self-checking analyzer system 200.

Of course, as with the previous example, the validity of the 90% watercut measurement also could be validated by comparing it with the watercut percentage that corresponds to the measured frequency of the water oscillator 103. In other words, the percentages are compared rather than the frequencies.

In some embodiments, the self-checking analyzer system 200 would be self-checking at every measurement interval typically less than three seconds apart. In other embodiments, the calibrations curves could be stored as polynomial equations or as a table for later interpolation in the field for real time measurement.

Although the above embodiments show a specific number of salt water curves at specific salinities, one of ordinary skill in the art would recognize that any number of salt water curves at any number of salinities, such as 0.3%, 0.5%, 1%, 5%, and 8%, may be utilized without departing from the scope and spirit of this disclosure.

In a further embodiment, an additional test can be made during calibration by recording the frequency response or reflected power/insertion loss of the oil oscillator 101 and/or the water oscillator 103 when only air is in the measurement unit 201. These frequencies can be stored in a memory of the self-checking analyzer system 200 and recalled at a later time to compare against frequencies obtained in the field when an operator is able to obtain free air in the measurement unit 201. This becomes a further validity check on the integrity of the self-checking analyzer system 200. The frequency response or reflected power/insertion loss of the oil oscillator 101 and/or the water oscillator 103 when only air is in the measurement unit 201 is used alone or in conjunction with the values from the calibration curves as a validity check on the integrity of the self-checking analyzer system 200.

Figure 9A:
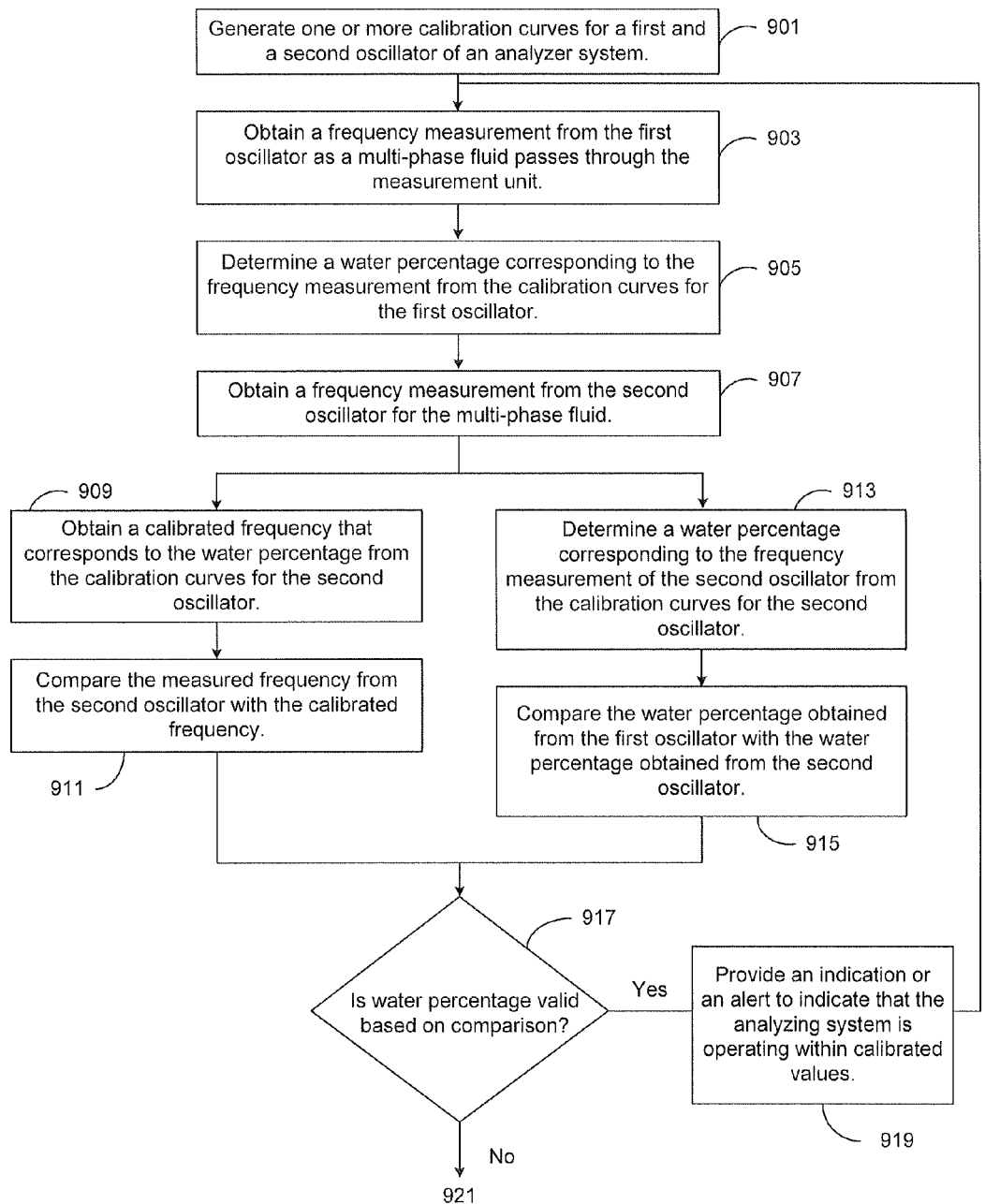
FIGS. 9A and 9B illustrate a method of validating a measurement from an analyzer system.
Figure 9B:
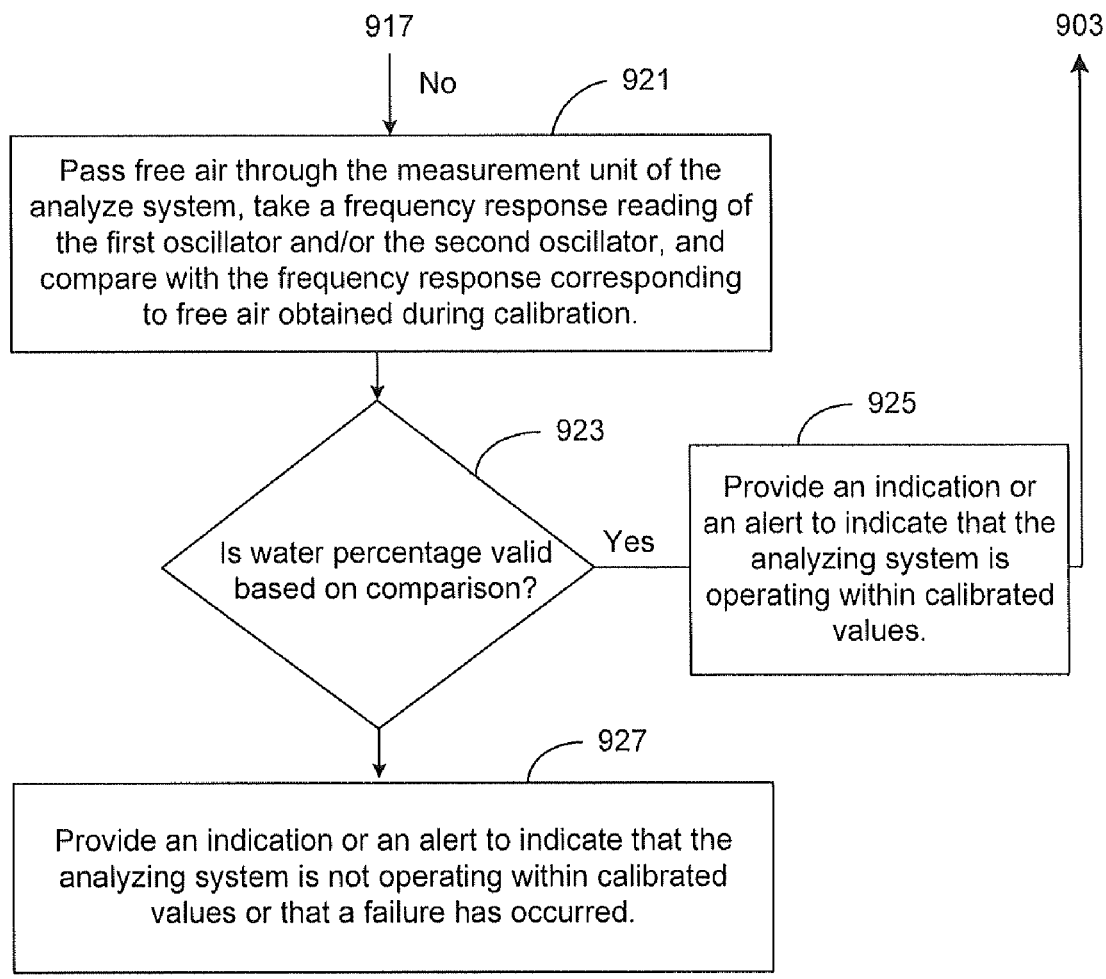

FIGS. 9A and 9B illustrate a method of validating a measurement from an analyzer system.

In this embodiment, one or more calibration curves are generated for a first and a second oscillator of an analyzer system (Block 901).

The calibration curves may include oil emulsion curves and salt water emulsion curves, for example, at 0.1%, 3%, and 11% salt. The calibration curves also may include the frequency response of the first and/or second oscillators with only air in the measurement unit of the analyzer system. The first and second oscillators are independent of one another in terms of their tuning elements, active devices, and/or matching circuitry. For example, the first oscillator could be an oil oscillator while the second oscillator is a water oscillator. Accordingly, the first and second oscillators will differ in their frequency response.

A frequency measurement is then obtained from the first oscillator as a multi-phase fluid passes through the measurement unit (Block 903). A water percentage corresponding to the frequency measurement is then determined from the calibration curves for the first oscillator (Block 905).

A frequency measurement is then obtained from the second oscillator for the multi-phase fluid (Block 907). A calibrated frequency that corresponds to the water percentage obtained from the first oscillator is obtained from the calibration curves for the second oscillator (Block 909). The measured frequency from the second oscillator is then compared to the calibrated frequency (Block 911).

Alternatively or in addition to, after a frequency measurement is obtained from the second oscillator for the multi-phase fluid (Block 907), a water percentage corresponding to the frequency measurement of the second oscillator is then determined from the calibration curves for the second oscillator (Block 913). The water percentage obtained from the first oscillator is then compared with the water percentage obtained from the second oscillator (Block 915).

The method then determines if the water percentage obtained from the first oscillator is valid based upon the comparison of the water percentages or frequency responses (Block 917). If the water percentage from the first oscillator is valid, an indication or an alert is provided to indicate that the analyzing system is operating within calibrated values (Block 919), and the method returns to Block 903 to obtain another frequency measurement from the first oscillator. If the water percentage from the first oscillator is not valid, a frequency response of the first oscillator and/or the second oscillator to free air is taken and compared with the frequency response to free air obtained during calibration (Block 921).

The method then determines if the water percentage obtained from the first oscillator is valid based upon the comparison of the frequency responses to free air (Block 923). If the water percentage from the first oscillator is valid, an indication or an alert is provided to indicate that the analyzing system is operating within calibrated values (Block 925), and the method returns to Block 903 to obtain another frequency measurement from the first oscillator. If the water percentage from the first oscillator is not valid, an indication or an alert is provided to indicate that the analyzing system is not operating within calibrated values or that a failure has occurred (Block 927). In some embodiments, the method could either stop taking frequency measurements at this point until further input by the operator is received or continue to obtain another frequency measurement from the first oscillator.

Of course, in some embodiments, if the water percentage obtained from the first oscillator is not valid based upon the comparison of the water percentages or frequency responses (Block 917), the method skips Blocks 921 to 925 and provides an indication or alert without comparing the frequency responses to free air (Block 927).

Figure 10A:
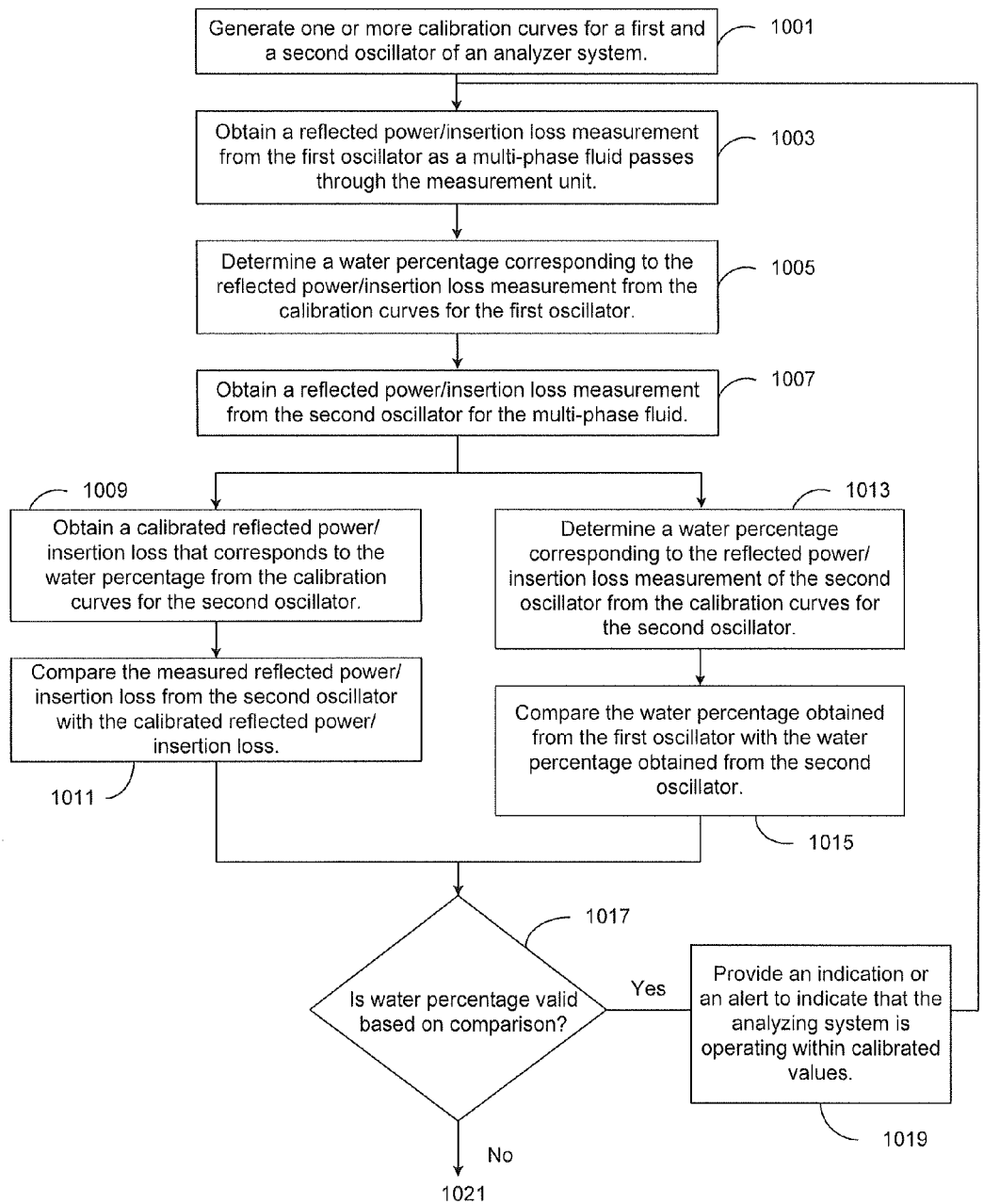
FIGS. 10A and 10B illustrate another method of validating a measurement from an analyzer system.
Figure 10B:
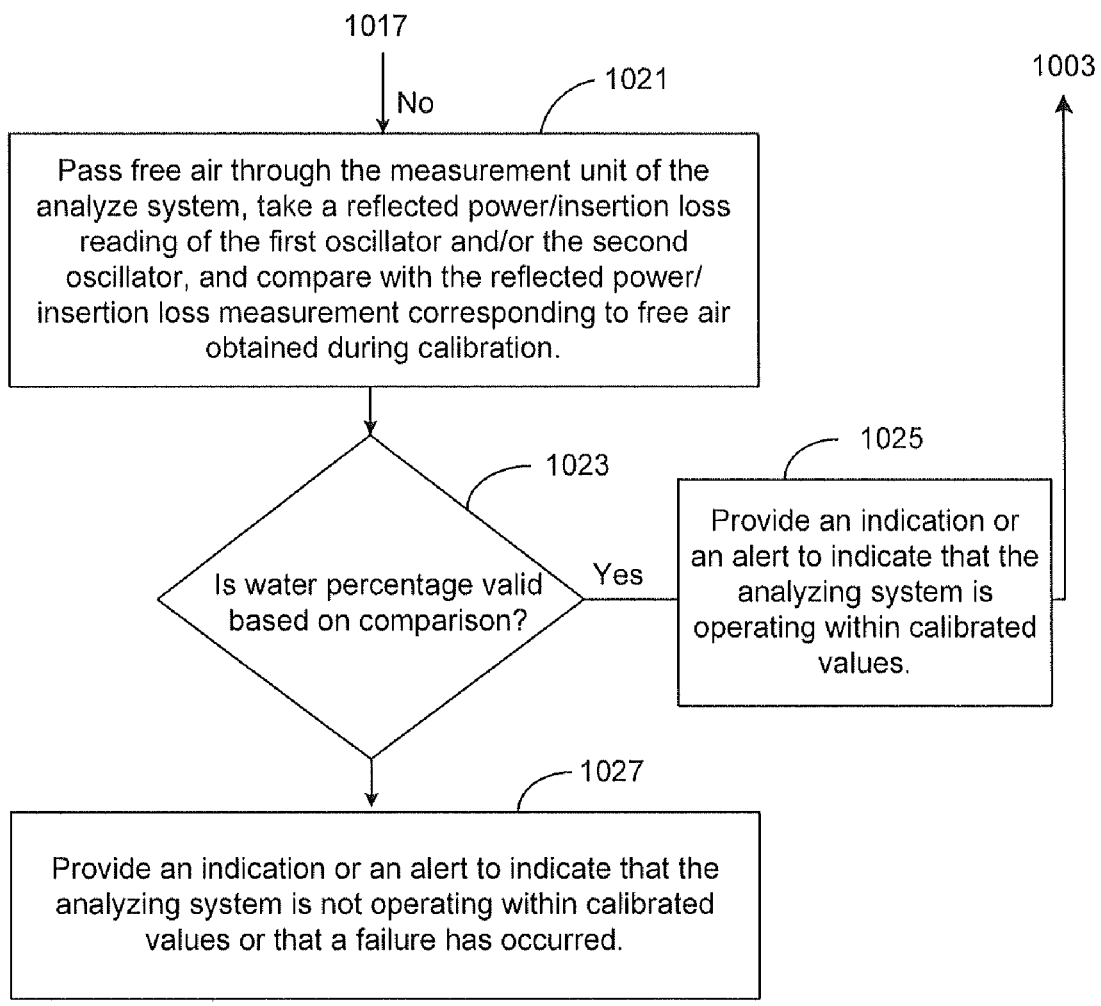

FIGS. 10A and 10B illustrate another method of validating a measurement from an analyzer system.

In this embodiment, one or more calibration curves are generated for a first and a second oscillator of an analyzer system (Block 1001).

The calibration curves may include oil emulsion curves and salt water emulsion curves, for example, at 0.1%, 3%, and 11% salt. The calibration curves also may include reflected power/insertion loss measurement of the first and/or second oscillators with only air in the measurement unit of the analyzer system. The first and second oscillators are independent of one another in terms of their tuning elements, active devices, and/or matching circuitry. For example, the first oscillator could be an oil oscillator while the second oscillator is a water oscillator. Accordingly, the first and second oscillators will differ in their frequency response.

A reflected power/insertion loss measurement is obtained from the first oscillator as a multi-phase fluid passes through the measurement unit (Block 1003). A water percentage corresponding to the reflected power/insertion loss measurement is then determined from the calibration curves for the first oscillator (Block 1005).

A reflected power/insertion loss measurement is then obtained from the second oscillator for the multi-phase fluid (Block 1007). A reflected power/insertion loss measurement that corresponds to the water percentage obtained from the first oscillator is obtained from the calibration curves for the second oscillator (Block 1009). The measured reflected power/insertion loss from the second oscillator is then compared to the calibrated reflected power/insertion loss (Block 1011).

Alternatively or in addition to, a water percentage corresponding to the reflected power/insertion loss measurement from the second oscillator loss is then determined from the calibration curves for the second oscillator (Block 1013). The water percentage obtained from the first oscillator is then compared to the water percentage obtained from the second oscillator (Block 1015).

The method then determines if the water percentage obtained from the first oscillator is valid based upon the comparison of the water percentages or reflected power/insertion loss measurements (Block 1017). If the water percentage from the first oscillator is valid, an indication or an alert is provided to indicate that the analyzing system is operating within calibrated values (Block 1019), and the method returns to Block 1003 to obtain another reflected power/insertion loss measurement from the first oscillator. If the water percentage from the first oscillator is not valid, a reflected power/insertion loss measurement of the first oscillator and/or the second oscillator corresponding to free air is taken during operation and compared to the reflected power/insertion loss measurement corresponding to free air obtained during calibration (Block 1021).

The method then determines if the water percentage obtained from the first oscillator is valid based upon the comparison of the reflected power/insertion loss measurements corresponding to free air (Block 1023). If the water percentage from the first oscillator is valid, an indication or an alert is provided to indicate that the analyzing system is operating within calibrated values (Block 1025), and the method returns to Block 1003 to obtain another reflected power/insertion loss measurement from the first oscillator. If the water percentage from the first oscillator is not valid, an indication or an alert is provided to indicate that the analyzing system is not operating within calibrated values or that a failure has occurred (Block 1027).

In some embodiments, the method could either stop taking reflected power/insertion loss measurements at this point until further input by the operator is received or continue to obtain another reflected power/insertion loss measurement from the first oscillator.

Of course, in some embodiments, if the water percentage obtained from the first oscillator is not valid based upon the comparison of the water percentages or reflected power/insertion loss measurements (Block 1017), the method skips Blocks 1021 to 1025 and provides an indication or alert without comparing the reflected power/insertion loss measurements to free air (Block 1027).

Figure 11:
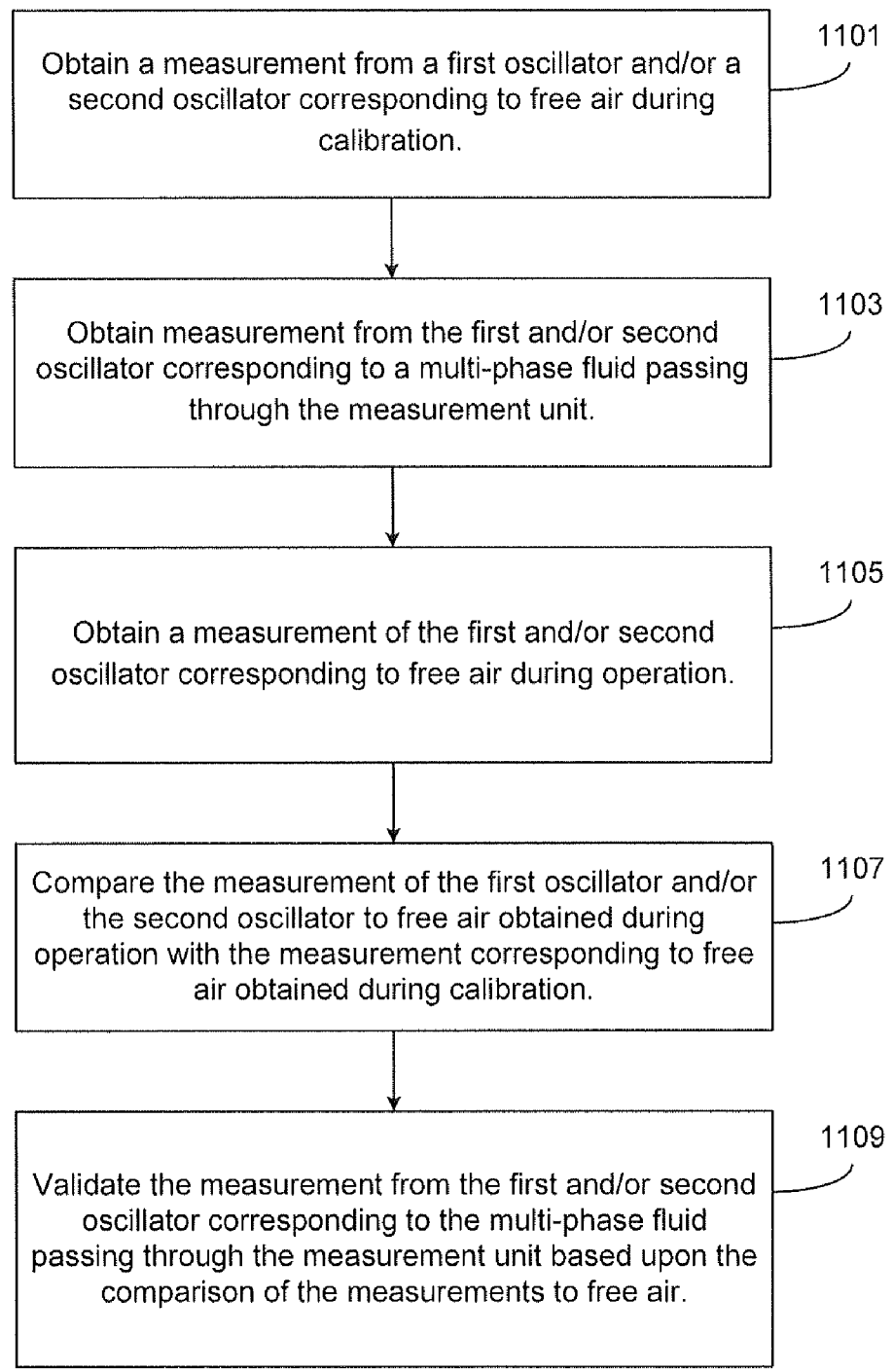
FIG. 11 illustrates yet another method of validating a measurement from an analyzer system.

FIG. 11 illustrates yet another method of validating a measurement from an analyzer system.

In this embodiment, a reflected power/insertion loss measurement or a frequency response of a first oscillator and/or a second oscillator corresponding to free air is obtained during calibration (Block 1101).

During operation, a reflected power/insertion loss measurement or a frequency response is obtained from the first and/or second oscillator as a multi-phase fluid passes through the measurement unit (Block 1103). A reflected power/insertion loss measurement or a frequency response of the first and/or second oscillator corresponding to free air also is obtained during operation (Block 1105). The frequency response or reflected power/insertion loss measurement of the first oscillator and/or the second oscillator to free air obtained during operation is compared with the frequency response to free air obtained during calibration (Block 1107).

The method then validates the frequency or reflected power/insertion loss measurement from the first oscillator and/or second oscillator as the multi-phase fluid passed through the measurement unit based upon the comparison of the frequency or reflected power/insertion loss measurements corresponding to free air (Block 1109).

Although FIGS. 9 to 11 illustrate examples of a method for validating a measurement from an analyzer system, various changes may be made to FIGS. 9 to 11. For example, while shown as a series of steps, various steps in FIGS. 9 to 11 could overlap, occur in parallel, occur in a different order, or occur multiple times. Further, note that these steps could occur at any suitable time, such as in response to a command from a user or external device or system.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A measurement unit comprising:
   a first measuring device;
   a second measuring device differing in frequency response from the first measuring device;
   a switch; and
   an antenna element,
   wherein the switch is configured to connect the first measuring device to the antenna element to obtain a first reflected power/insertion loss measurement corresponding to a fluid flow and to connect the second measuring device to the antenna element to obtain a second reflected power/insertion loss measurement corresponding to the fluid flow, and
   wherein the measurement unit is configured to validate the first reflected power/insertion loss measurement by comparing a first value of the first reflected power/insertion loss measurement with a corresponding value of the second reflected power/insertion loss measurement.

2. The measurement unit of claim 1, wherein the first measuring device is one of an oil oscillator and a water oscillator and the second first measuring device is the other.

3. The measurement unit of claim 1, wherein the first measuring device is configured to measure a characteristic of a first component of the fluid flow and the second measuring device is configured to measure a characteristic of a second component of the fluid flow.

4. The measurement unit of claim 1, wherein the measurement unit is further configured to validate the first reflected power/insertion loss measurement by comparing a reflected power/insertion loss measurement of the first measuring device corresponding in free air with a calibrated value for free air.

5. The measurement unit of claim 1, wherein the first reflected power/insertion loss measurement is used to determine a water content of the fluid flow.

6. The measurement unit of claim 5, wherein the water content is derived from one or more calibration curves.

7. An analyzer system comprising:
   a pipeline for receiving a fluid flow;
   a first measuring device configured to provide a first reflected power/insertion loss measurement corresponding to the fluid flow; and
   a second measuring device differing in frequency response from the first measuring device and configured to provide a second reflected power/insertion loss measurement corresponding to the fluid flow,
   wherein the analyzer system is configured to validate the first reflected power/insertion loss measurement by comparing a first value of the first reflected power/insertion loss measurement with a corresponding value of the second reflected power/insertion loss measurement.

8. The system of claim 7, wherein the first measuring device is one of an oil oscillator and a water oscillator and the second first measuring device is the other.

9. The system of claim 7, wherein the first reflected power/insertion loss measurement is used to determine a water content of the fluid flow.

10. The system of claim 7, wherein the water content is derived from one or more calibration curves.

11. The system of claim 7, wherein the analyzer system is further configured to validate the first reflected power/insertion loss measurement by comparing a reflected power/insertion loss measurement of the first measuring device corresponding in free air with a calibrated value for free air.

12. The system of claim 7 further comprising:
    a switch configured to connect the first measuring device to an antenna element to obtain the first reflected power/insertion loss measurement and to connect the second measuring device to the antenna element to obtain the second reflected power/insertion loss measurement.

13. The system of claim 12, wherein the first measuring device is configured to measure a characteristic of a first component of the fluid flow and the second measuring device is configured to measure a characteristic of a second component of the fluid flow.

14. A method of validating a reflected power/insertion loss measurement comprising:
    obtaining a first reflected power/insertion loss measurement corresponding to a fluid flow using a first measuring device;
    obtaining a second reflected power/insertion loss measurement corresponding to the fluid flow using a second measuring device, the second measuring device differing in frequency response from the first measuring device; and
    validating the first reflected power/insertion loss measurement by comparing a first value of the first reflected power/insertion loss measurement with a corresponding value of the second reflected power/insertion loss measurement.

15. The method of claim 14, wherein the first measuring device is one of an oil oscillator and a water oscillator and the second first measuring device is the other.

16. The method of claim 14 further comprising:
    validating the first reflected power/insertion loss measurement by comparing a reflected power/insertion loss measurement of the first measuring device corresponding in free air with a calibrated value for free air.

17. The method of claim 14, wherein the first and second measuring devices differ from one another in at least one of tuning elements, active devices, and matching circuitry.

18. The method of claim 14 further comprising:
    determining a first water content of the fluid flow using the first reflected power/insertion loss measurement.

19. The method of claim 18 further comprising:
    determining a second water content of the fluid flow using the second reflected power/insertion loss measurement; and
    validating the first water content using the second water content.

20. The method of claim 19, wherein the first and second water contents are determined from one or more calibration curves.

* * * * *